(12) United States Patent
Brown

(10) Patent No.: US 6,782,643 B2
(45) Date of Patent: Aug. 31, 2004

(54) ORTHOTIC INSERT HAVING HEEL POST WITH CONTOURED LOWER SURFACE

(76) Inventor: Dennis N Brown, 6867 Holeman Ave., Blaine, WA (US) 98230

( * ) Notice: Subject to any disclaimer, the term of this patent is extended or adjusted under 35 U.S.C. 154(b) by 2 days.

(21) Appl. No.: 10/165,543

(22) Filed: Jun. 7, 2002

(65) Prior Publication Data

US 2003/0226288 A1 Dec. 11, 2003

(51) Int. Cl.⁷ .............................. A61F 5/14; A43B 7/16
(52) U.S. Cl. ............................ 36/144; 36/173; 36/178; 36/92
(58) Field of Search .................... 36/144, 143, 173, 36/178, 44, 92, 36 R, 71, 176, 80, 81

(56) References Cited

U.S. PATENT DOCUMENTS

| | | | | |
|---|---|---|---|---|
| 4,800,657 A | * | 1/1989 | Brown | 36/44 |
| RE33,648 E | * | 7/1991 | Brown | 36/44 |
| 5,146,698 A | * | 9/1992 | Tilles et al. | 36/44 |
| 5,842,294 A | * | 12/1998 | Fabricant | 36/144 |
| 6,286,232 B1 | * | 9/2001 | Snyder et al. | 36/44 |
| 6,481,120 B1 | * | 11/2002 | Xia et al. | 36/44 |
| 6,536,137 B1 | * | 3/2003 | Celia | 36/44 |
| 6,625,906 B2 | * | 9/2003 | Mayer et al. | 36/30 R |

FOREIGN PATENT DOCUMENTS

WO          WO 2/09214 A1 *  6/1992    ........... A43B/13/40

* cited by examiner

Primary Examiner—Anthony D. Stashick
(74) Attorney, Agent, or Firm—Todd N. Hathaway

(57) ABSTRACT

An orthotic insert having an angled lateral surface that engages the insole so as to pivot the insert in a lateral direction and invert the rearfoot at heel strike, and a medial bottom surface that freely interfits within the heel counter and insole of the shoe so as to avoid limiting pivoting motion in the medial direction as the weight on the foot shifts forwardly and medially. Pivoting motion in the medial direction is arrested by engagement between a distal medial portion of the rigid plate member and the insole along the transverse plane of the shoe. The distal medial portion of the plate member is located generally proximal and beneath the first metatarsal head of the foot. The upwardly angled medial surface of the post permits the post to fit optimally within the heel area of the shoe and also avoids interference between the heel counter/insole and the post that would impair proper operation of the insert.

20 Claims, 3 Drawing Sheets

ORTHOTIC INSERT HAVING HEEL POST WITH CONTOURED LOWER SURFACE

BACKGROUND OF THE INVENTION a. Field of the Invention

The present invention relates generally to orthotic devices for use in shoes, and, more particularly, to an orthotic insert having a heel post with an angled lower surface of the lateral side for controlling angulation in a lateral direction at heel strike and a rigid plate member with a distal medial portion for controlling angulation in a medial direction as the foot progresses towards toe-off.

b. Related Art

Orthotic inserts have long been employed to treat conditions or otherwise enhance the functions of the human foot, whether for ordinary walking or for various forms of specialized activities, such as skiing, skating, running and so on.

A particular category of these devices employs a built-up structure in which there is a generally rigid, but still somewhat resilient flexible plate for supporting the plantar surface of the foot, and a thick, vertical post which is mounted to the heel end of the plate. Typically, the orthotic plate is constructed of a somewhat thin, generally rigid material, such as glass- or graphite-fiber/resin composite materials, polyurethane, molded plastics or the like. The post, in turn, is frequently formed of a generally hard but somewhat compressively yielding material, such as hard rubber, molded urethane, Neoprene or methyl methacrylate, which is capable of supporting the rear foot under the loads that are developed at heel strike.

Such devices are generally intended to both correctly position the foot at heel strike and control the motions of the foot as it progresses through the stance phase of the gait cycle from heel strike towards toe-off. The insert also provides or madates a range of motion in the joints of the foot. For example, a normal foot should roll (frontal plane motion) about 4°–6° when walking. To control the motion of the foot, the plate member flexes resiliently to a controlled degree, and frequently there is also a need to impart a degree of rocking or eversion/inversion motion at the heel post as well, depending on the needs of the individual foot and the intended use. For example, it is often desirable to position the foot so as to increase inversion at heel contact, so as to increase the total amount of pronation and therefore the total amount of motion which is available for the balance of the gait cycle.

In order to provide the desired degree of inversion at heel strike, common practice in the prior art has been to form the heel post with a flat bottom that extends parallel to the transverse plane of the foot and insole. Material is then ground or otherwise removed from the bottom of the heel post on the lateral side. For example, FIG. 3 shows an exemplary prior art orthotic device 10 having a rigid plate 12 and raised heel post 14. A portion of the flat bottom surface 16 has been ground off to form an angled secondary surface 18 on the lateral side of the post. This provides the post with a "bi-planar" bottom which is intended to pivot the post through a controlled angle $\theta_0$, from a first position in which the mean bottom surface 16 rests flat on the transverse plane 20, to a second position in which the upwardly-angled lateral surface 18 rests on the insole. The rocking motion of the heel post is imparted to the plate member 10 which is mounted to the top of the post, the plate member being the component which actually bears against and engages the plantar surface of the person's foot. Thus, the post inverts the rearfoot at heel strike, when the weight is borne mostly on the lateral side of the heel, as indicated at 22 in FIG. 2. Then, as indicated by dotted line 24, the weight shifts forwardly and medially as the foot progresses through the gait cycle. As the weight shifts onto the medial side of the foot, as indicated at 26 in FIG. 2, the post is intended to pivot medially and return the device to the initial orientation shown in FIG. 3.

For several reasons, the operation of prior art devices of this type has frequently been unsatisfactory. For example, as can be seen in FIG. 4, the insole 30 and heel counter 32 of a conventional shoe are usually convexly curved in order to accommodate the heel. As a result, the edges of the bi-planar post tend to dig into and "hang up" on the sides of the heel counter/insole, especially along the medial and lateral edges 34, 36. This impairs the ability of the post to produce the desired rocking motion, to the point that deep wear areas often develop where the edges of the post press into and rub against the material of the heel counter.

As can be seen in FIG. 4, the flat bottom 16 and the tendency of the edges to hang up on the sides of the counter/insole also tend to prevent the post from fitting all the way down into the shoe, so that a significant gap 38 is left between the insole and the bottom of the device. This causes the heel of the orthotic to sit excessively high in the heel of the shoe and creates user discomfort. Moreover, the unpredictable engagement between the post and counter/insole often causes the post to become tilted one way or another and out of proper alignment with respect to the transverse plane, so that even if the device is able to rock back and forth in the shoe it is unable to develop the desired angulation and range of motion.

Practitioners have resorted to various expediencies in an effort to address these problems. For example, it is common to attempt to "custom fit" the device to the interior of the shoe by grinding away additional material along the perimeter of the post and/or gradually increasing the angle of the lateral plane until the desired degree of motion is achieved. However, this requires considerable tedious work, and unless great care is exercised too much material may be removed so that the device must be discarded. In other instances, practitioners have resorted to filling in the heel area of the insole in order to provide a raised, flat surface for the medial plane of the post, referred to as a "heel raise" but this is again an expensive and time-consuming process, and also modifies the shoe so that in some instances it can no longer be used without the orthotic insert.

Still further, even in installations where the device ends up functioning as intended, the results have often been less than ideal from a biomechanical standpoint. For example, employing the flat medial surface of the post to control the range of motion creates an abrupt stop to the rocking motion as the weight of the foot shifts to the medial side. This is quite noticeable and somewhat uncomfortable to the wearer, and also counteracts the normal shock-absorbing function of the foot as it pronates. In some instances designers have attempted to compensate for this problem by using a softer, more flexible material for the orthotic plate, however, the reduction in rigidity tends to compromise the structural integrity of the plate and its ability to properly support and control the motions of the foot. Moreover, the abrupt stop tends to cause the material of the plate to flex excessively in the area just forward of the distal medial edge of the post (see area 40 in FIG. 1); over time, the flexing causes the plate to develop cracks in this area, which is a principle cause of failure of orthotic inserts of this type.

Accordingly, there exists a need for an orthotic insert having a heel post, in which the heel post fits into the curved insole and heel counter of the shoe without impairing the desired pivoting motion of the insert. Furthermore, there exists a need for such an orthotic insert in which the bottom of the post fits down into the shoe without hanging up on the sides of the heel counter/insole, so that the insert does not sit excessively high within the shoe. Still further, there exists a need for such an orthotic insert which does not create an abrupt stop to the pivoting motion in the medial direction, as the weight of the foot is transferred to medial side of the insert, so as to provide enhanced shock-absorption characteristics and reduce structural damage to the rigid plate of the insert. Still further, there exists a need for such an orthotic insert having a heel post that can be manufactured and used in a standardized form, and that does not require expensive and time-consuming custom fitting for use in conventional shoes.

SUMMARY OF THE INVENTION

The present invention has solved the problems cited above, and is an orthotic insert for removable placement in shoe having an insole and a heel counter. Broadly, the orthotic insert comprises: (a) a substantially rigid plate member for engaging a plantar surface of a foot and having a heel end and a forefoot portion, the forefoot portion extending forwardly to at least proximal a metatarsal head area of the foot and having a distal medial portion for engaging the insole substantially along a transverse plane of the shoe, and (b) a heel post having an upper end mounted to a heel end of the plate member and a lower end extending downwardly therefrom, the lower end of the heel post comprising (i) a generally planar lateral bottom surface that extends upwardly and laterally at a predetermined angle for engaging the insole of the shoe so as to provide angular placement and limit pivoting motion of the heel post in the lateral direction, and (ii) a medial bottom surface that extends generally upwardly and medially for freely interfitting with the insole and heel counter so as to avoid the limiting pivoting motion of the heel post in the medial direction, so that the lateral bottom surface of the heel post engages the insole of the shoe so as to arrest pivoting motion of the orthotic insert in the lateral direction as weight is borne on a lateral side of the foot at heel strike, and the distal medial portion of the plate member engages the insole so as to arrest pivoting motion of the insert in the medial direction as weight is shifted to a medial side of a foot as the foot progresses through a gait cycle.

The lower end of the heel post may further comprise a generally planar central bottom surface intermediate the medial and lateral bottom surfaces that extends generally parallel to the transverse plane for engaging the insole so as to stabilize the orthotic insert within the shoe and provide a more gentle transition in the rolling motion.

The medial bottom surface of the heel post may comprise a generally planar medial bottom surface that extends upwardly and medially from the central bottom surface. The planar medial bottom surface and the planar lateral bottom surface may extend upwardly at approximately equal angles to the transverse plane.

The medial bottom surface of the heel post may have a generally convex contour for freely interfitting with the insole and heel counter. The generally convex contour may comprise a substantially continuous curved surface or one or more generally planar surfaces.

The distal medial portion of the rigid plate member may be located proximate a first metatarsal head of the foot. The distal medial portion of the plate member may comprise a forward edge portion of the plate member, and the forward edge of the rigid plate member may generally follow a line of metatarsal heads of the foot.

The present invention also provides a heel post for mounting to a substantially rigid plate member of an orthotic insert, the rigid plate member having a heel end and a forefoot portion extending to at least proximal a metatarsal head area of the foot and having a distal medial portion for engaging the insole of the shoe substantially along a transverse plane of the shoe. The heel post comprises (a) an upper end for being mounted to the heel end of the rigid plate member, and (b) a lower end for extending downwardly from the heel end of the rigid plate member, the lower end of the heel post comprising a generally planar lateral bottom surface that extends laterally and upwardly for engaging the insole so as to provide angular placement and limit pivoting motion of the heel post in a lateral direction, and a medial bottom surface that extends generally upwardly and medially for freely interfitting with the insole and heel counter so as to avoid limiting pivoting motion of the heel post in the medial direction.

The lower end of the heel post may further comprise a generally planar central bottom surface intermediate the medial and lateral surfaces that extends generally parallel to the transverse plane for engaging the insole so as to stabilize the orthotic insert within the shoe and provide a more gentle transition in the rolling motion.

The medial bottom surface of the heel post may comprise a generally planar medial bottom surface that extends upwardly and medially from the planar bottom surface. The generally planar medial bottom surface and the generally planar lateral bottom surface may extend upwardly at approximately equal angles to the transverse plane, and the upper end of the heel post may be configured for interchangeable mounting to rigid plate members for use with right and left feet.

The medial bottom surface of the heel post may have a generally convex contour for freely interfitting with the insole and heel counter of the shoe. The generally convex contour of the medial bottom surface of the heel post may comprise a substantially continuous curved surface, or may comprise one or more generally planar surfaces.

These and other features and advantages of the present invention will be apparent from a reading of the following detailed description with reference to the accompanying drawings.

DETAILED DESCRIPTION

The present invention provides an orthotic insert having an angled heel post with a medial lower surface that extends upwardly and medially and is shaped to accommodate the curved surface of the insole and heel counter on the medial side. Unlike prior art devices, the post does not have a flat, horizontal lower surface on its medial side for arresting rocking motion of the insert in the medial direction.

As part of the present invention, it has been discovered that the configuration of prior art inserts has been based on the incorrect assumption that a flat lower surface on the medial side of the post was necessary in order to limit the rocking motion of the insert to the prescribed range. In other words, it has been assumed that the flat surface on the medial side of the post was necessary in order to arrest pivoting motion in the medial direction as weight was transferred forwardly and medially on the foot, and that without the flat surface on the medial side the pivoting motion would go beyond the proper angle and the foot would overpronate.

However, Applicant has discovered that, provided the distal (forward) edge of the rigid plate member extends to the metatarsal head area of the foot, the rigidity of the plate member itself can be used to arrest the pivoting motion of the insert in the medial direction. This is because the first metatarsal head (large toe) of the foot presses the distal-medial edge portion of the plate more-or-less directly against the transverse plane as the foot moves beyond about the 25% point of the stance phase of the gait cycle.

Since the present invention therefore employs the distal medial edge portion of the plate member to arrest pivoting motion in the medial direction, rather than the lower surface of the heel post, the medial lower surface of the heel post can be provided with a contour that freely interfits with the curved heel counter and insole of the shoe. The upwardly angled plane remains on the lateral surface of the post, but the medial surface is free to be upwardly angled, beveled, undercut or rounded as desired.

Figure 5:
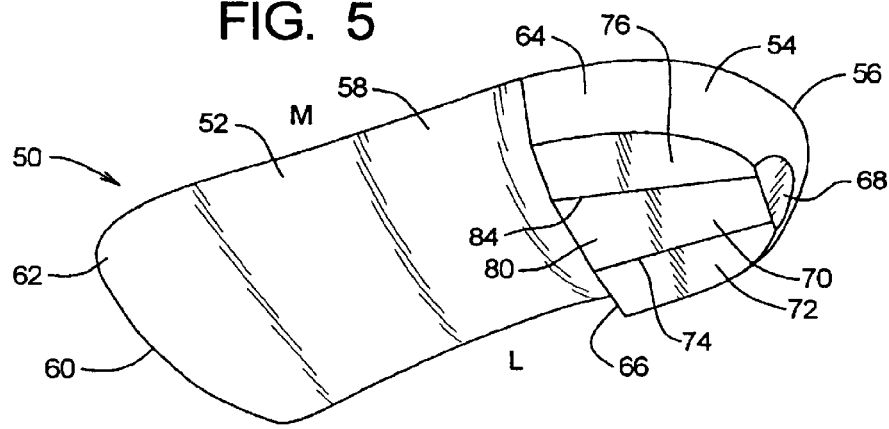
FIG. 5 is a bottom, perspective view of an orthotic insert in accordance with the present invention, looking upwardly and forwardly along the medial side of the insert and showing the upwardly extending lower surface on the medial side of the heel post thereof.
Figure 6:
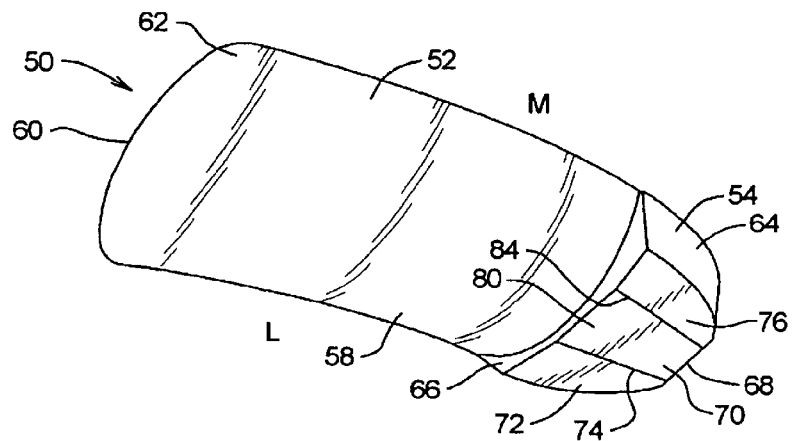
FIG. 6 is a bottom, perspective view of the orthotic insert of FIG. 5, looking upwardly and rearwardly along the medial side thereof.

Accordingly, FIGS. 5–6 show an orthotic insert 50 in accordance with the present invention, which includes a generally rigid, resiliently flexible plate member 52 having a post member 54 mounted at its heel end. The plate member may be formed of any suitable, preferably thin material having sufficient strength and rigidity to support the foot, combined with a degree of resilient flexibility, such as, for example, glass fiber-resin, graphite fiber-resin or other fiber-resin materials or combinations thereof, or polyurethane, polypropylene or various molded plastics or metal. A combination of laminated glass fiber-resin and graphite fiber-resin materials is eminently suitable for use in the preferred embodiment of the invention. As will be discussed in greater detail below, however, the improved dynamic characteristics provided by the heel post of the present invention enables the plate member to be made of more rigid and durable materials, or materials having better shock-absorbing qualities, than might be used in the plate members of prior art inserts.

The rigid plate member 52 is configured to engage the wearer's foot over most of its length, and therefore has a heel end 56, midfoot portion 58, and a forward edge 60. The upper surface of the rigid plate member is contoured to engage the plantar surface of the wearer's foot, and may include any of a variety of structural features intended to control or improve the functions of the foot.

Figure 7:
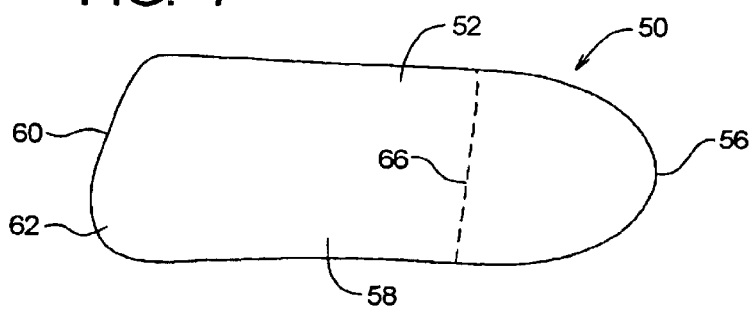
FIG. 7 is a top, plan view of the orthotic insert of FIGS. 5–6, looking towards the upper surface of the rigid plate member of the insert, with the forward edge of the underlying post being indicated by dotted line image.

As can be seen in FIG. 7, the forward edge 60 of the plate member is preferably angled forwardly towards the medial side and generally follows the line of the metatarsal heads (i.e., the area beneath the metatarsal heads of the five phalanges) of the foot, with the medial-distal edge portion 62 being configured to be located proximate the first metatarsal head, at the base of the large toe. In the preferred embodiment, the forward edge 60 of the plate member extends just behind the metatarsal heads themselves, so as to receive the downward pressure thereof without causing discomfort under the ball of the foot. It will be understood, however, that in some embodiments the forward edge of the plate may extend further beneath the metatarsal heads or even forwardly beneath the phalanges themselves, so long as the forefoot portion of the plate member includes the medial distal portion 62 that contacts the insole of the shoe as the weight is transferred to the medial side of the foot.

As can also be seen in FIGS. 5–7, the top (superior) side of the heel post member 54 is mounted at the rearward end of the plate member 52 by any suitable means, as by adhesive bonding, for example. The post member is a comparatively thick, downwardly extending member having a U-shaped perimeter 64 that extends around the heel end of the device and a transverse forward edge 66 that is preferably located forwardly of the heel cup and rearwardly of the midfoot/arch area of the plate member. A small forwardly and downwardly angled skive 68 is formed at the bottom of the perimeter 64 at the rearward end of the post member in order to accommodate the heel counters of shoes, which tend to slope forwardly in this area, although it will be understood that the skive may not be present in all embodiments. The post member may be formed of any suitable, generally rigid, preferably somewhat resiliently compressible material, such as hard rubber or cast urethane, for example, with thermoplastic rubber (TPR) being particularly suitable due to its durability and resilient cushioning qualities. These materials may be similar to those used in prior art posts, however, the improved dynamic characteristics of the orthotic insert of the present invention may permit the post member to be formed of a material having greater rigidity or durability, or other desired characteristics, as compared with the post members of prior art devices. The post member may be solid, or may be hollow or include one or more chambers for cushioning or other purposes.

The bottom (inferior) side 70 of the post member includes an upwardly angled surface 72 on its lateral side. The angled surface 72 has a ridge-like lower edge 74 that is located towards the longitudinal centerline of the insert, and extends laterally and upwardly at a predetermined angle to the transverse plane. The upwardly angled lateral surface is therefore generally similar in shape and location to the corresponding angled surface on the bottom of the prior art posts described above, although the improved interfit with the shoe that is provided by the present invention permits the angle to be more precisely controlled; in the illustrated example, the lateral surface 72 is angled upwardly at 6° to the transverse plane, for use in a typical walking application.

Figure 8:
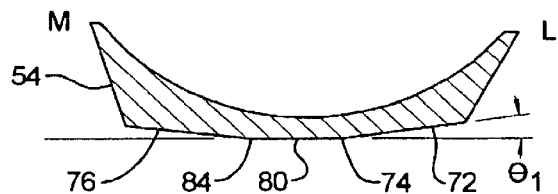
FIG. 8 is a cross-sectional view of the heel post of the orthotic insert of FIGS. 5–6, showing the angled lower surface on the medial side thereof.

Unlike the prior art posts, however, the bottom 70 of the post member has an upwardly extending surface 76 on its medial side as well, rather than a flat lower surface parallel to the transverse plane. The upwardly extending medial surface accommodates the rounded, concave contour of the heel counter and insole, thus providing an improved interfit between the two and avoiding the problem of the edges of the post "hanging up" on the sides of the counter/insole as described above. In the embodiment which is illustrated in FIGS. 5–7 and also FIG. 8, the medial surface 76 of the post is formed as a generally planar surface that extends upwardly and medially from a lower edge 84, at an angle to the transverse plane similar to that of the lateral surface 72. A comparatively narrow, flat intermediate surface 80 is formed near the center line of the post, between the angled medial and lateral surfaces, and extends generally parallel to the transverse plane; the intermediate surface serves to make the rolling motion of the device more gentle and less abrupt and also provides the device with a degree of stability and makes it feel less "tippy" when resting in the shoe, although it will be understood that this surface does not arrest the pivoting motion of the insert in the manner of the medial heel surface of the prior art post which is described above.

Since the primary purpose of the upwardly and medially extending medial surface of the post member is to accommodate and provide clearance for the heel counter/insole of the shoe, so as to avoid contact and interference between the two, it may have any suitable configuration that provides requisite clearance, although planar or generally convex contours are generally preferred for strength, structural integrity and durability. However, a particular advantage of the generally planar medial surface 76 is that in some embodiments this can be configured to extend upwardly at the same or similar angle (relative to the transverse plane) as the angled surface 72 on the lateral side of the post. This allows the same post member to be interchangeably mounted to plate members for right or left feet, reducing tooling, manufacture, inventory and labor costs. In such embodiments, the resilient material in the upper portion of the post member, in combination with the reduced thickness near the upper edge of the perimeter wall 64, can provide a degree of flexibility that permits the upper part of the post to conform to the subtly different bottom contours of plate members for right and left feet. Alternately, a deformable filler may be used between the top of the post and the bottom of the plate member, or the post may be provided with one or more pads, ridges or other structures for mounting to the undersides of the plate members while accommodating the different contours. Furthermore, the lower surface of the plate members themselves may be provided with contours or structures for facilitating the interchangeable mounting of the post members.

It will be understood, however, that in many embodiments separate posts will be provided that are specifically contoured for use with plate members for the right and left feet. Furthermore, certain of above features, particularly the flexible upper edges of the heel post, may also be used to aid in mounting standardized posts to custom-made plate members in such embodiments where the posts are not interchangeable between right and left feet.

Figure 9:
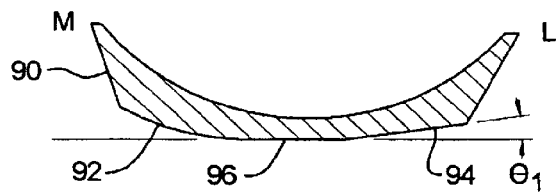
FIG. 9 is a cross-sectional view, similar to FIG. 7, showing an embodiment in which the lower medial surface of the post is formed as a curved rather than planar or multi-planar surface.

FIG. 9 shows an embodiment in which the post 90 has a lower medial surface 92 that is smoothly curved or rounded, rather than planar. This provides a convex contour for interfitting with the insole/heel counter of the shoe without interfering with the pivoting motion of the insert. The lower lateral surface 94, in turn, is angled upwardly by an angle $\theta_1$ in substantially the same manner as in the embodiment illustrated in FIG. 8, in order to provide the desired rearfoot angulation at heel strike. Similar to the embodiment illustrated in FIG. 8, the smoothly contoured medial surface may include a comparatively flat panel or spot 96 near the longitudinal center line for providing a more gentle rolling motion and reducing the sense of "tippiness".

Figure 1:
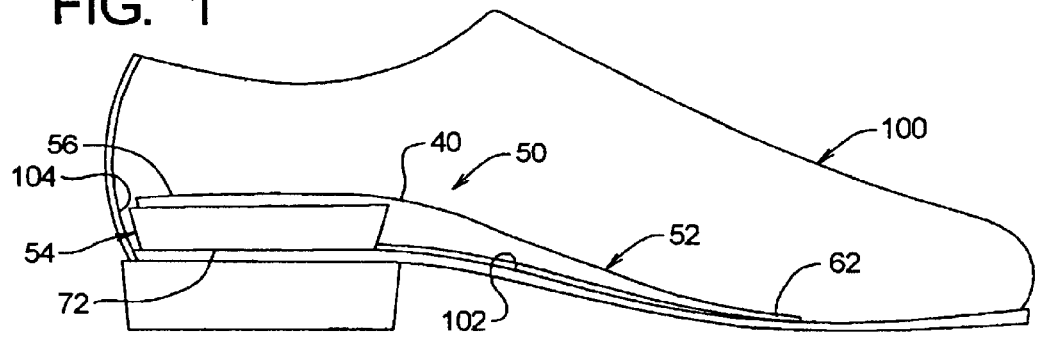
FIG. 1 is an elevational, cutaway view of an orthotic insert in accordance with the present invention, showing the manner in which this is installed in an exemplary shoe.
Figure 2:
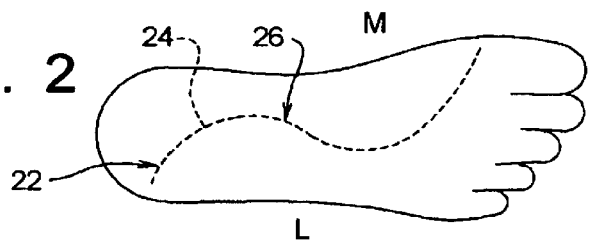
FIG. 2 is a plan, somewhat schematic view of a human foot, looking downwardly from the top of the foot, showing the path by which weight on the foot is transferred in forward and medial directions as the gait cycle progresses from heel strike towards toe-off.
Figure 3:
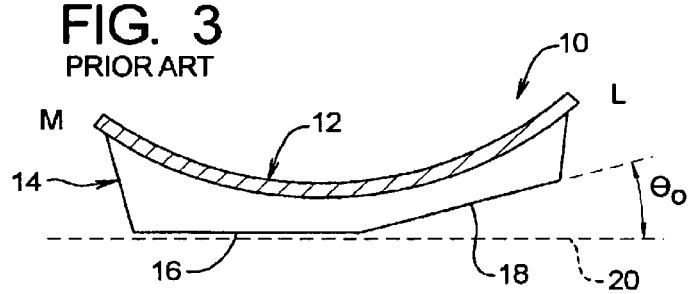
FIG. 3 is a cross-sectional view of a prior art form of orthotic insert having a heel post, looking forwardly from the rear of the device, showing the bi-planar bottom of the post having a horizontal surface extending parallel to the transverse plane on the medial side and an upwardly-angled planar surface on the lateral side.
Figure 4:
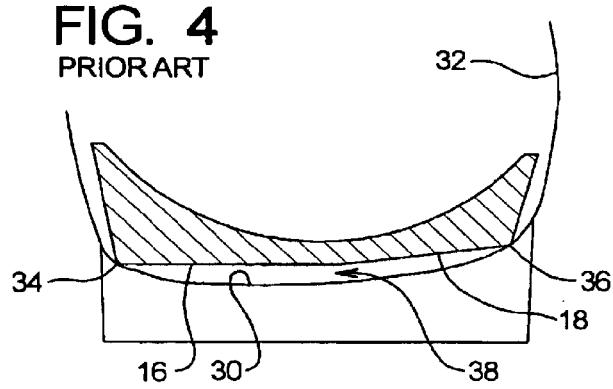
FIG. 4 is a cross-sectional view of the heel portion of the prior art orthotic insert of FIG. 3 installed in a shoe, showing the manner in which the edges of the post tend to bear against and hang up on the sides of the heel counter and insole, and also the manner in which the post tends to become improperly aligned in the shoe.
Figure 10:
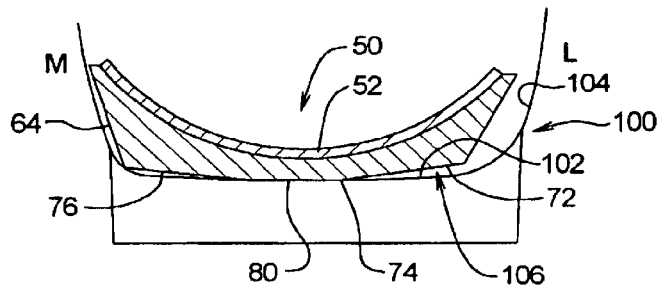
FIG. 10 is a cross-sectional view of the heel post of FIG. 8, showing the post installed in a shoe and in an initial orientation prior to heel strike and the manner in which the rounded heel counter and insole of the shoe accommodate and interfit with the contoured medial bottom surface of the post.
Figure 11:
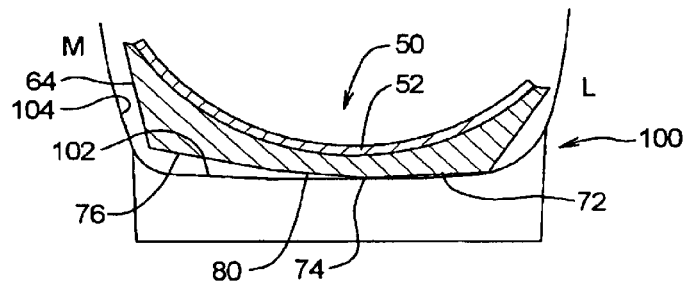
FIG. 11 is a cross-sectional view of the heel post of FIG. 9, showing the manner in which the upwardly-angled surface on the lateral side of the post pivots downwardly to engage the insole so as to provide the rearfoot with the desired degree of inversion at heel strike.

FIGS. 10–11 show the heel post 54 of the embodiment of FIGS. 5–8 installed in an exemplary shoe 100 having a conventional insole 102 and heel counter 104 (see also FIG. 1). As can be seen in FIG. 10, the upwardly and medially extending medial bottom surface 76 enables the post to sit fully down in the shoe without hitting or "hanging up" on the insole or heel counter, so that the lowermost surface 80 of the post rests atop the insole and there is no underlying gap as in the prior art devices. This, in turn, positions the lateral surface 72 of the post member at the proper angle relative to the insole, and ensures that there is sufficient space 106 for the angled surface to pivot downwardly through the desired range motion before engaging the insole.

Accordingly, when weight is placed on the lateral side of the post at heel strike as described above, the angled lateral surface 72 of the post pivots downwardly to the insole so as to provide the heel with the desired amount of inversion (e.g., 4°–6°). As this is done, the ridge 74 or other juncture at the bottom of the angled surface 72 provides a fulcrum for the pivoting motion. Then, as weight is shifted forwardly and medially on the foot, the post and the rigid plate 52 pivot medially back to the position shown in FIG. 10. As stated above, motion in this direction is arrested at the desired limit by the engagement between the insole and the distal medial area 62 of the plate member, not by the medial lower surface of the post. Therefore, as can be seen in FIG. 10, a small gap 110 will usually remain between the medial surface 76 of the post when in the medially pivoted position, although in some installations there may be some minimal contact between the post and the insole/heel counter in this area.

Because the present invention uses the medial distal portion of the plate to limit the medial pivoting motion, rather than the underside of the post, the pivoting motion is arrested in a somewhat more gradual manner than in prior art devices. This reduces the shock imparted to the foot by the insert and to some extend alleviates the need for the plate member to serve a shock-absorbing function, so that if desired the plate member may be formed of a more rigid and potentially more durable material than in prior devices. Conversely, if desired, the flexibility of the plate member can be maintained or even increased when using the post of the present invention, so that the flexing length of the medial border is increased and, in conjunction with the gradual stop at the medial limit of motion, shock absorption, durability and user comfort are further enhanced.

Since the heel post of the present invention eliminates the need for custom fitting to match the contours of the shoe, the post can be produced and supplied in a standardized form for mounting to the rigid orthotic plates. For example, the posts may be produced in a standard shape to fit plates for a predetermined range of foot sizes, e.g., a first post for sizes 6–7, another for 8–9, another for 10–11, and so on. The plates themselves may also be standardized, or in some instances may be semi-custom or custom-formed for an individual foot.

It is to be recognized that various alterations, modifications, and/or additions may be introduced into the constructions and arrangements of parts described above without departing from the spirit or ambit of the present invention as defined by the appended claims.

What is claimed is:

1. An orthotic insert for removable placement in a shoe having an insole and a heel counter, said orthotic insert comprising:
   a substantially rigid plate member for engaging a plantar surface of a foot and having a heel end and a forefoot portion, said forefoot portion extending forwardly to at least proximal a metatarsal head area of said foot and having a distal medial portion for engaging said insole substantially along a transverse plane of said shoe; and
   a heel post having an upper end mounted to said heel end of said plate member and a lower end extending downwardly therefrom, said lower end of said heel post comprising:
      a generally planar lateral bottom surface that extends upwardly and laterally from said transverse plane, at a predetermined angle for engaging said insole so as to provide angular placement and limit pivoting motion of said heel post in a lateral direction; and
      a medial bottom surface that extends generally upwardly and medially from said transverse plane for freely interfitting with said insole and heel counter so as to avoid limiting pivoting motion of said heel post in a medial direction;
      so that said lateral bottom surface of said heel post engages said insole so as to arrest pivoting motion of said orthotic insert in said lateral direction as weight is borne on a lateral side of said foot at heel strike, and said distal medial portion of said plate member engages said insole so as to arrest pivoting motion of said orthotic insert in said medial direction as weight is shifted to a medial side of said foot as said foot progresses through a gait cycle.

2. The orthotic insert of claim 1, wherein said lower end of said heel post further comprises:
   a generally planar central bottom surface intermediate said medial and lateral bottom surfaces that extends generally parallel to said transverse plane for engaging said insole so as to stabilize said orthotic insert within said heel counter of said shoe and provide a gentle transition in said pivoting motion.

3. The orthotic insert of claim 2, wherein said medial bottom surface of said heel post has a generally convex contour for freely interfitting with said insole and heel counter.

4. The orthotic insert of claim 3, wherein said generally convex contour of said medial bottom surface of said heel post comprises a substantially continuous curved surface.

5. The orthotic insert of claim 2, wherein said medial bottom surface of said heel post comprises one or more generally planar surfaces.

6. The orthotic insert of claim 2, wherein said medial bottom surface of said heel post comprises a generally planar medial bottom surface that extends upwardly and medially from said planar central bottom surface.

7. The orthotic insert of claim 6, wherein said generally planar medial bottom surface and said generally planar lateral bottom surface extend upwardly at approximately equal angles to said transverse plane.

8. The orthotic insert of claim 1, wherein said distal medial portion of said rigid plate member is located proximate a first metatarsal head of said foot.

9. The orthotic insert of claim 8, wherein said distal medial portion of said rigid plate member comprises a forward edge portion of said plate member.

10. The orthotic insert of claim 9, wherein said rigid plate member comprises a forward edge that generally follows a line of metatarsal heads of said foot.

11. A heel post for mounting to a substantially rigid plate member of an orthotic insert, said rigid plate member having a heel end and a forefoot portion extending to at least proximal a metatarsal head area of a foot and having a distal medial portion for engaging an insole of a shoe substantially along a transverse plane of said shoe, said heel post comprising:
   an upper end for being mounted to said heel end of said rigid plate member; and
   a lower end for extending downwardly from said heel end of said rigid plate member, said lower end of said heel post comprising:
      a generally planar lateral bottom surface that extends upwardly and laterally from said transverse plane, at a predetermined angle for engaging said insole so as to provide angular placement and limit pivoting motion of said heel post in a lateral direction; and
      a medial bottom surface that extends generally upwardly and medially from said transverse plane for freely interfitting with said insole and heel counter so as to avoid limiting pivoting motion of said heel post in a medial direction;
      so that said lateral bottom surface of said heel post engages said insole so as to arrest pivoting motion of said orthotic insert in said lateral direction as weight is borne on a lateral side of said foot at heel strike, and said distal medial portion of said plate member engages said insole so as to arrest pivoting motion of said orthotic insert in said medial direction as weight is shifted to a medial side of said foot as said foot progresses through a gait cycle.

12. The heel post of claim 10, wherein said lower end of said heel post further comprises:
   a generally planar central bottom surface intermediate said medial and lateral bottom surfaces that extends generally parallel to said transverse plane for engaging said insole so as to stabilize said orthotic insert within said heel counter of said shoe and provide a gentle transition in said pivoting motion.

13. The heel post of claim 12, wherein said medial bottom surface of said heel post has a generally convex contour for freely interfitting with said insole and heel counter.

14. The heel post of claim 13, wherein said generally convex contour of said medial bottom surface of said heel post comprises a substantially continuous curved surface.

15. The heel post of claim 13, wherein said generally convex contour of said medial bottom surface of said heel post comprises one or more generally planar surfaces.

16. The heel post of claim 14, wherein said medial bottom surface of said heel post comprises a generally planar medial bottom surface that extends upwardly and medially from said planar central bottom surface.

17. The heel post of claim 16, wherein said generally planar medial bottom surface and said generally planar lateral bottom surface extend upwardly at approximately equal angles to said transverse plane.

18. The heel post of claim 17, wherein said upper end of said heel post is configured for interchangeable mounting to rigid plate members for use with right and left feet.

19. An orthotic insert for removable placement in a shoe having an insole and a heel counter, said orthotic insert comprising:

a substantially rigid plate member for engaging a plantar surface of a foot and having a heel end and a forefoot portion extending forwardly to proximal a metatarsal head area of said foot, said forefoot portion having a forward edge that generally follows a line of metatarsal heads of said foot and a distal medial portion proximate a first metatarsal head of said foot for engaging said insole substantially along a transverse plane of said shoe; and a heel post having an upper end mounted to said heel end of said plate member and a lower end, said lower end extending downwardly therefrom of said heel post comprising:

a generally planar lateral bottom surface that extends upwardly and laterally from said transverse plane, for engaging said insole so as to provide angular placement and limit pivoting motion of said heel post in a lateral direction;

a generally planar medial bottom surface that extends generally upwardly and medially from said transverse plane for freely interfitting with said insole and heel counter so as to avoid limiting pivoting motion of said heel post in a medial direction; and a generally planar central bottom surface that extends generally parallel to said transverse plane intermediate said lateral and medial bottom surfaces for engaging said insole so as to stabilize said heel post within said heel counter of said shoe and provide a gentle transition in said pivoting motion;

so that said lateral bottom surface of said heel post engages said insole so as to arrest pivoting motion of said orthotic insert in said lateral direction as weight is borne on a lateral side of said foot at heel strike, and said distal medial portion of said plate member engages said insole so as to arrest pivoting motion of said orthotic insert in said medial direction as weight is shifted to a medial side of said foot as said foot progresses through a gait cycle.

20. The orthotic insert of claim 19, wherein said lateral and medial bottom surfaces extend upwardly at approximately equal angles to said transverse plane.

* * * * *